(12) United States Patent
Drumond et al.

(10) Patent No.: US 10,517,514 B2
(45) Date of Patent: Dec. 31, 2019

(54) GLYCEMIC RESPONSE INSIGHT DETECTION

(71) Applicant: Verily Life Sciences LLC, Mountain View, CA (US)

(72) Inventors: Miguel Angelo Drumond, Oakland, CA (US); Nikhil Roy, Sunnyvale, CA (US); Cara Leggett Silver, San Francisco, CA (US); Aaron Haywood Stoertz, Redwood City, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/786,920

(22) Filed: Oct. 18, 2017

(65) Prior Publication Data

US 2019/0110723 A1 Apr. 18, 2019

(51) Int. Cl.
  *A61B 5/145* (2006.01)
  *A61B 5/00* (2006.01)
  *G06F 19/00* (2018.01)
  *G09B 19/00* (2006.01)

(52) U.S. Cl.
  CPC ........ *A61B 5/14532* (2013.01); *A61B 5/0022* (2013.01); *G06F 19/3418* (2013.01); *G06F 19/3475* (2013.01); *G09B 19/0092* (2013.01)

(58) Field of Classification Search
  CPC .............. A61B 5/14532; G16H 40/00
  See application file for complete search history.

(56) References Cited

U.S. PATENT DOCUMENTS

| | | | |
|---|---|---|---|
| 8,690,578 B1 * | 4/2014 | Nusbaum | G09B 19/00 |
| | | | 128/905 |
| 8,803,688 B2 | 8/2014 | Yim et al. | |
| 2010/0075353 A1 | 3/2010 | Heaton | |
| 2013/0190583 A1 | 7/2013 | Grosman et al. | |
| 2017/0053084 A1 * | 2/2017 | McMahon | A61M 5/142 |

FOREIGN PATENT DOCUMENTS

WO 2017011346 A1 1/2017

* cited by examiner

*Primary Examiner* — Sheetal R Paulson
(74) *Attorney, Agent, or Firm* — Perkins Coie LLP

(57) ABSTRACT

Introduced here are techniques for developing personalized retroactive insights into how contextual factors can affect glycemic responses. The personalized retroactive insights can be made available to the corresponding individual so that they can examine the impact certain contextual events have had on blood glucose level. A contextual event represents an activity or a circumstance that is related to glycemic response. Rather than state the absolute amount of certain molecules (e.g., carbohydrates, protein, or fat) in a foodstuff, an insight detection platform can instead interpret disparate data types to discover the effect certain contextual events have on blood glucose level.

14 Claims, 6 Drawing Sheets

400

401
Acquire physiological data

402
Analyze the physiological data to identify a variation

403
Acquire contextual data

404
Analyze the contextual data to identify a contextual event related to the variation

405
Identify a personalized retrospective insight by linking the variation and the contextual event

406
Create a historical record of personalized retrospective insights

501
Access a historical record of personalized retrospective insights associated with an individual

502
Monitor contextual data associated with the individual

503
Discover a contextual event similar to a past contextual event

504
Calculate a measure indicative of an expected glycemic response to the contextual event

505
Cause a notification to be presented to the individual that specifies the expected glycemic response

FIG. 5

GLYCEMIC RESPONSE INSIGHT DETECTION

TECHNICAL FIELD

Various embodiments concern techniques for developing insights into the contextual factor(s) that influence changes in the physiological state of an individual.

BACKGROUND

After ingestion of a foodstuff that contains carbohydrates, the human body breaks down the carbohydrates into glucose. The breaking down of carbohydrates can yield monosaccharides and disaccharides, most of which is glucose. Glucose serves as a source of energy for the cells of the human body.

Glucose is transported via circulation within the blood stream. Therefore, ingestion of foodstuffs will influence the concentration of glucose within the blood stream (also referred to as the "blood glucose level" or "glucose level"). However, other factors may also influence the blood glucose level of an individual. For example, participation in physical activities may affect how quickly carbohydrates are broken down into glucose.

The term "glycemic response" refers to the rate at which ingested foodstuffs are able to increase the blood glucose level and the length of time the blood glucose level remains elevated. It is normal for the blood glucose level to rise after eating and then fall after fasting over a short period of time. While several tools have been developed to help quantify the effect of certain foodstuffs on blood glucose level, these tools suffer from numerous drawbacks.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 4 depicts a flow diagram of a process for discovering the correspondence between glycemic responses and contextual events.

FIG. 5 depicts a flow diagram of a process for promoting changes in behavior based on personalized retrospective insights identified by an insight detection platform.

Figure 1:
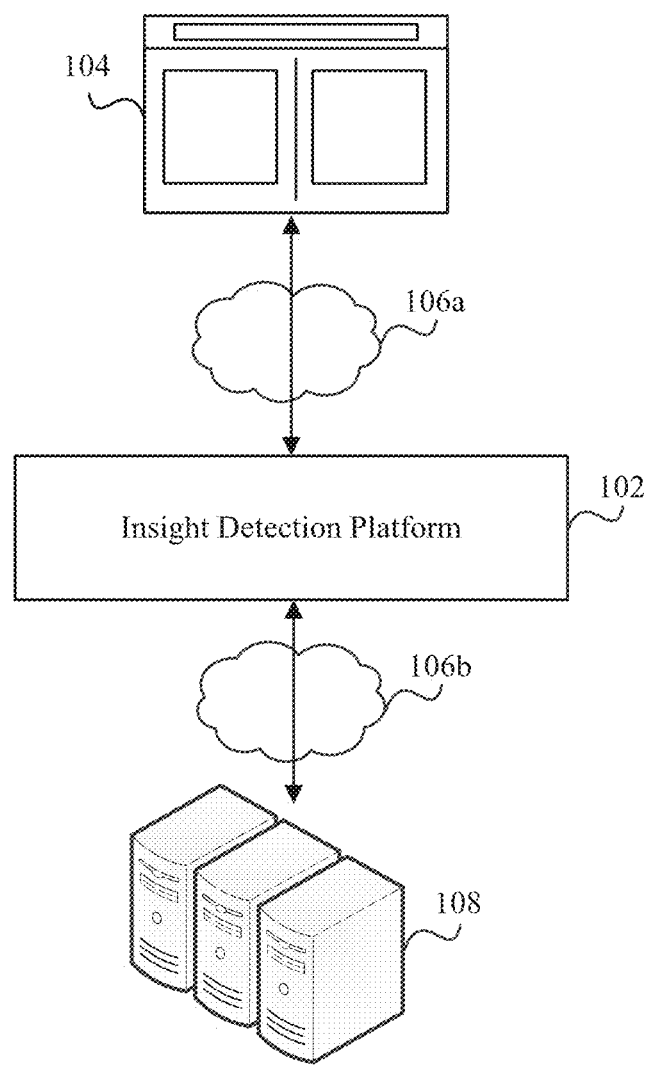
FIG. 1 illustrates a network environment that includes an insight detection platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

After ingestion of a foodstuff that contains carbohydrates, the human body breaks down the carbohydrates into glucose. The breaking down of carbohydrates can yield monosaccharides and disaccharides, most of which is glucose. Glucose is transported via circulation within the blood stream. Therefore, ingestion of foodstuffs will influence the concentration of glucose within the blood stream.

Diabetes mellitus (commonly referred to as "diabetes") is a group of metabolic disorders in which there are high blood glucose levels over a prolonged period. If left untreated, diabetes can cause many complications. For example, long-term complications can include cardiovascular disease, stroke, chronic kidney disease, foot ulcers, and damage to the eyes.

Individuals with diabetes can benefit from education about treatment, good nutrition to achieve a normal body weight, and exercise. However, those individuals often find it difficult to implement lifestyle changes that promote healthier blood glucose levels. For example, when an individual with diabetes consumes a foodstuff, the foodstuff can have a detrimental impact from a glycemic response perspective. But the negative effect(s) are often not apparent to the individual until it is too late. For instance, the individual may not discover that their pancreas is unable to keep up with sugar intake until long-term complications begin to appear.

Introduced here, therefore, are techniques for developing personalized retroactive insights into how contextual factors can affect glycemic responses. The personalized retroactive insights can be made available to the corresponding individual so that they can examine the impact certain foodstuffs have had on blood glucose level. The term "foodstuff" refers to any type of food or beverage.

Rather than state the absolute amount of certain molecules (e.g., carbohydrates, protein, or fat) in a foodstuff, a computer program can be configured to interpret disparate data types to calculate the effect consumption of a certain foodstuff has had on blood glucose level. For example, the computer program may parse several data types to discover a contextual event related to a glycemic response.

A contextual event represents an activity or a circumstance that is related to the glycemic response. More specifically, a contextual event can describe a time window with classifiable characteristic(s) that can be indicated by device-captured contextual information from one or more information channels. These classifiable characteristic(s) can be instantaneous, within a constant timeframe, or within a flexible timeframe. A flexible timeframe could be discovered by parsing metadata generated by a network-enabled device associated with an individual. For example, the computer program may examine metadata indicative of network-enabled device use defined by instances of waking/sleeping the network-enabled device (e.g., a mobile phone).

Thus, a contextual event will describe the particular context of a glycemic response. Contextual events can be discovered by examining data acquired from one or more sources. Examples of data include:

Physiological data related to a physiological condition of an individual. For example, physiological data specifying blood glucose level could be generated by a glucose monitoring device (e.g., a continuous glucose monitor or a blood glucose meter).

Foodstuff data related to an identity or a quantity of foodstuff(s) consumed by an individual. In some embodiments, foodstuff data is generated after performing image recognition process(es) on images of foodstuff(s) taken by the individual. In other embodiments, the foodstuff data is generated in response to the individual self-reporting which foodstuff(s) have been consumed.

Location data related to the location of an individual. For example, location data could be generated by a computing device (e.g., a mobile phone) associated with the individual. A computer program may also examine the location data to identify other activities. For example, if the individual spends a specified amount of time near a geographical location associated with a specified restaurant, then the computer program may establish that the individual likely consumed foodstuff(s) at the specified restaurant.

Activity data related to activities performed by an individual. For example, activity data could be generated by a fitness tracker that monitors steps and/or specific activities.

Medication data related to medication event(s) involving an individual. For example, medication data could be generated by a healthcare database (e.g., a pharmacy database or a hospital database) that is accessible via an application programming interface (API). As another example, medication data could be generated by a medication device that monitors administrations of medication. Thus, a medication event could be refilling a prescription, administering a medication, etc.

Engagement data related to activities indicative of engagement with an electronic device. For example, a computing device (e.g., a mobile phone) operated by an individual may create a record of browsing activities, calling activities, messaging activities, application activities (e.g., documenting social media usage), etc.

A computer program can be configured to identify personalized retroactive insights (e.g., correspondences) between changes in physiological data and contextual events detected within these other types of data. These personalized retroactive insights advantageously describe how the human body of an individual uniquely reacts to contextual events.

The computer program may also create a historical record of these personalized retroactive insights. In such embodiments, the computer program can automatically predict how the individual is likely to react to future contextual events of a particular kind. More specifically, if the computer program determines that the individual has begun experiencing a contextual event similar to a past contextual event, then the computer program can estimate the likely effect of the contextual event on blood glucose level. Personalized retroactive insights could also be presented to the individual as biofeedback to promote changes in behavior to improve health.

Embodiments may be described with reference to particular computer programs, system configurations, networks, etc. However, those skilled in the art will recognize that the features described herein are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for developing personalized insights into how a glycemic response is affected by contextual event(s), predicting an expected glycemic response, generating notifications that specify the expected glycemic response, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, two devices may be electrically or communicatively coupled to one another despite not sharing a physical connection.

When used in reference to a list of multiple items, the word "or" is intended to cover all of the following interpretations: any of the items in the list, all of the items in the list, and any combination of items in the list.

Technology Overview

FIG. 1 illustrates a network environment 100 that includes an insight detection platform 102. Users can interface with the insight detection platform 102 via an interface 104. The insight detection platform 102 may be responsible for parsing physiological data to detect changes exceeding a specified threshold, as well as creating interfaces through which users can manage or view physiological data. Physiological data could, for example, specify the blood glucose level of a user accessing the interface 104 or some other person. For example, in some embodiments the interface 104 enables an individual with diabetes to view their own physiological data, while in other embodiments the interface 104 enables an individual (e.g., a family member or a medical professional, such as a physician or nurse) to view physiological data associated with another person.

The insight detection platform 102 may reside in a network environment 100. Thus, the insight detection platform 102 may be connected to one or more computer networks 106a-b. The computer network(s) 106a-b can include local area networks (LANs), wide area networks (WANs), metropolitan area networks (MANs), cellular networks, the Internet, etc.

The interface 104 is preferably accessible via some combination of a web browser, desktop software program, mobile application, or over-the-top (OTT) application. Accordingly, the interface 104 may be viewed on a personal computer, tablet computer, personal digital assistant (PDAs), mobile phone, game console (e.g., Sony PlayStation® or Microsoft Xbox®), music player (e.g., Apple iPod Touch®), wearable electronic device (e.g., a watch or fitness band), network-connected ("smart") device (e.g., a television or home assistant device), virtual/augmented reality system (e.g., a head-mounted display such as Oculus Rift® and Microsoft Hololens®), or some other electronic device.

Some embodiments of the insight detection platform 102 are hosted locally. That is, the insight detection platform 102 may reside on the computing device used to access the interface 104. Other embodiments of the insight detection platform 102 are executed by a cloud computing service operated by Amazon Web Services® (AWS), Google Cloud Platform™, Microsoft Azure®, or a similar technology. In such embodiments, the insight detection platform 102 may reside on a host computer server that is communicatively coupled (e.g., via a network) to one or more content computer servers 108. The content computer server(s) 108 can include different types of data, user information (e.g., profiles, credentials, and health-related information), and other assets. Additionally or alternatively, such information could be stored on the host computer server.

Certain embodiments are described in the context of network-accessible interfaces. However, those skilled in the art will recognize that the interfaces need not necessarily be accessible via a network. For example, a computing device may be configured to execute a self-contained software program that does not require network access. Instead, the self-contained software program may cause necessary assets (e.g., physiological data and contextual data) to be downloaded at a single point in time or on a periodic basis (e.g., hourly or daily).

Figure 2:
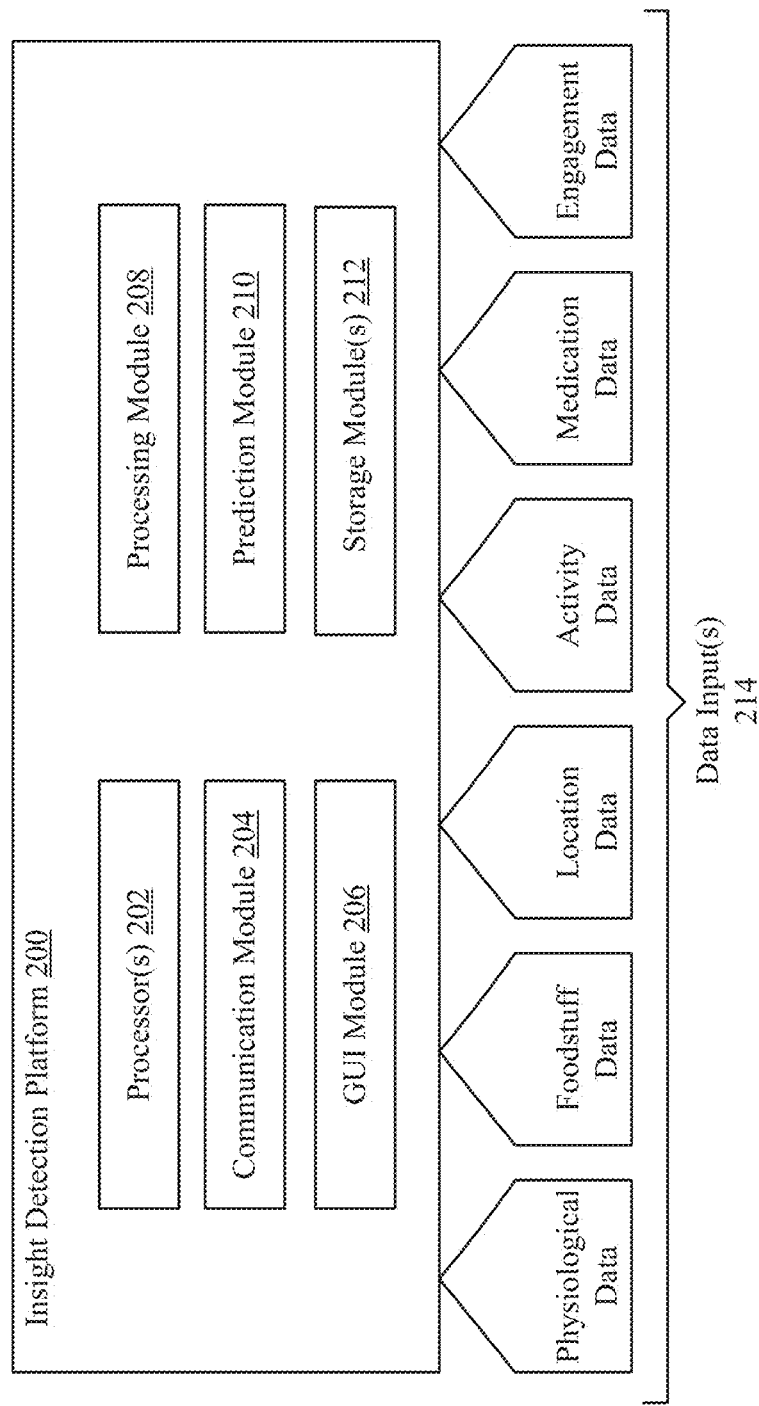
FIG. 2 depicts the high-level architecture of an insight detection platform for processing different types of data.

FIG. 2 depicts the high-level architecture of an insight detection platform 200 for processing different types of data. As shown in FIG. 1, an individual can interface with the insight detection platform 200 via an interface. The individual may be a person with diabetes or some other person with an interest in the blood glucose levels of the person with diabetes, such as a family member or a medical professional.

The insight detection platform 200 can include one or more processors 202, a communication module 204, a graphical user interface (GUI) module 206, a processing module 208, a prediction module 210, and one or more storage modules 212. In some embodiments a single storage module includes multiple computer programs for performing different operations (e.g., format conversion, temporal alignment, statistical analysis), while in other embodiments each computer program is hosted within a separate storage module. Embodiments of the insight detection platform 200 may include some or all of these modules/components, as well as other modules/components not shown here.

The processor(s) 202 can execute modules (e.g., the processing module 208 and the prediction module 210) from instructions stored in the storage module(s) 212, which can be any device or mechanism capable of storing information. The communication module 204 can manage communications between various components of the insight detection platform 200. The communication module 204 can also manage communications between a computing device on which the insight detection platform 200 resides and another computing device. For example, the communication module 204 may facilitate communication with various data sources through the use of application programming interfaces (APIs), bulk data interfaces, etc.

In some embodiments, the insight detection platform 200 resides on a computing device associated with an individual. For example, the insight detection platform 200 may reside on a mobile phone in the form of a mobile application. As further described below, the communication module 204 can facilitate the collection of data by communicating with one or more other computing devices across a network.

In other embodiments, the insight detection platform 200 resides on a computer server system. In such embodiments, the communication module 204 can communicate with a software program executing on the computing device associated with the individual. Those skilled in the art will recognize that the modules/components of the insight detection platform 200 can be distributed between the computer server system and the computing device associated with the individual in various manners. For example, some data (e.g., physiological data) may reside on the computing device of the individual, while other data (e.g., foodstuff data or activity data) may reside on the computer server system.

The GUI module 206 can generate the interface(s) that allow an individual to interact with the insight detection platform 200. For example, an interface may include a graph depicting physiological data over time, as well as suggestions for improving health (e.g., by performing certain activities, refraining from consuming certain foodstuffs, etc.).

The processing module 208 can apply one or more operations to data acquired by the insight detection platform 200. More specifically, the processing module 208 can interpret disparate data types to discover a contextual event related to a change in physiological data. A contextual event represents an activity or a circumstance that is related to the change in physiological data. For example, a contextual event may describe the particular context of a glycemic response.

The processing module 208 can discover contextual events by examining data acquired from one or more sources. Examples of data inputs 214 include:

Physiological data related to a physiological condition of an individual. For example, physiological data specifying blood glucose level could be generated by a glucose monitoring device (e.g., a continuous glucose monitor or a blood glucose meter).

Foodstuff data related to an identity or a quantity of foodstuff(s) consumed by an individual. In some embodiments, foodstuff data is generated after performing image recognition process(es) on images of foodstuff(s) taken by the individual. In other embodiments, the foodstuff data is generated in response to the individual self-reporting which foodstuff(s) have been consumed.

Location data related to the location of an individual. For example, location data could be generated by a computing device (e.g., a mobile phone) associated with the individual. A computer program may also examine the location data to identify other activities. For example, if the individual spends a specified amount of time near a geographical location associated with a specified restaurant, then the computer program may establish that the individual likely consumed foodstuff(s) at the specified restaurant.

Activity data related to activities performed by an individual. For example, activity data could be generated by a fitness tracker that monitors steps and/or specific activities.

Medication data related to medication event(s) involving an individual. For example, medication data could be generated by a healthcare database (e.g., a pharmacy database or a hospital database) that is accessible via an application programming interface (API). Thus, a medication event could be refilling a prescription, Engagement data related to activities indicative of engagement with an electronic device. For example, a computing device (e.g., a mobile phone) operated by an individual may create a record of browsing activities, calling activities, messaging activities, application activities (e.g., documenting social media usage), etc.

Timestamps or other metadata associated with any of the data inputs 214.

The processing module 208 can post-process some or all of the data received by the insight detection platform 200. For example, physiological data may be temporally aligned with activity data based on timestamp(s) identified within the physiological data and the activity data. As another example, location data can be statistically analyzed to detect instances of a certain event, such as a repeat visit to a restaurant. Thus, the processing module 208 can identify personalized retroactive insights between changes in these data inputs 214. In fact, the processing module 208 may add additional information (e.g., in the form of metadata) to data that enables linkages to be discovered between data of different types, from different sources, etc.

The processing module 208 can identify contextual events in several different ways.

First, some data inputs may only include a series of contextual events. For example, an image channel including uploaded images of meals or a medication channel indicating when medication was administered. Each channel includes a series of discrete contextual events that can be readily identified. Said another way, these contextual events represent binary contextual events (i.e., they either did occur or did not occur). The processing module 208 may be timestamps associated with these contextual events to identify correlation with other data inputs.

Second, other data inputs may include data that can be broken into predefined segments that represent contextual events. For example, an activity channel including activity data may be broken up into hour-long segments, each of which represents a discrete contextual event. The processing module 208 may examine the activity within each predefined segment to see whether there are measurable deviations, threshold exceedances, etc.

The data input(s) 214 typically include time series data having constant or varying spacing between successive entries (e.g., sensor readings). In some instances, the rule for determining whether a data input should generate a contextual event is well known (e.g., if activity level exceeds a certain threshold, then generate a contextual event). However, if correspondence between physiological data and a data input is ill-understood or unpredictable, then identifying contextual events can be very difficult. In such embodiments, the processing module 208 may perform freeform event detection based on batch algorithms, incremental algorithms, etc.

The processing module 208 may also create a historical record of personalized retroactive insights based on the correspondences between different types of data. In such embodiments, the prediction module 210 can automatically predict how an individual is likely to react to future contextual events of a particular kind. More specifically, the prediction module 210 can calculate the estimated effect that certain contextual event(s) will have on the physiological condition described by the physiological data. For example, if the physiological data specifies blood glucose level of an individual over time, then the prediction module 210 can determine how a contextual event (e.g., consuming a foodstuff, performing an athletic activity, or administering a medication) is likely to affect the blood glucose level. These predictions can be presented as biofeedback to promote changes in behavior to improve health.

Figure 3:
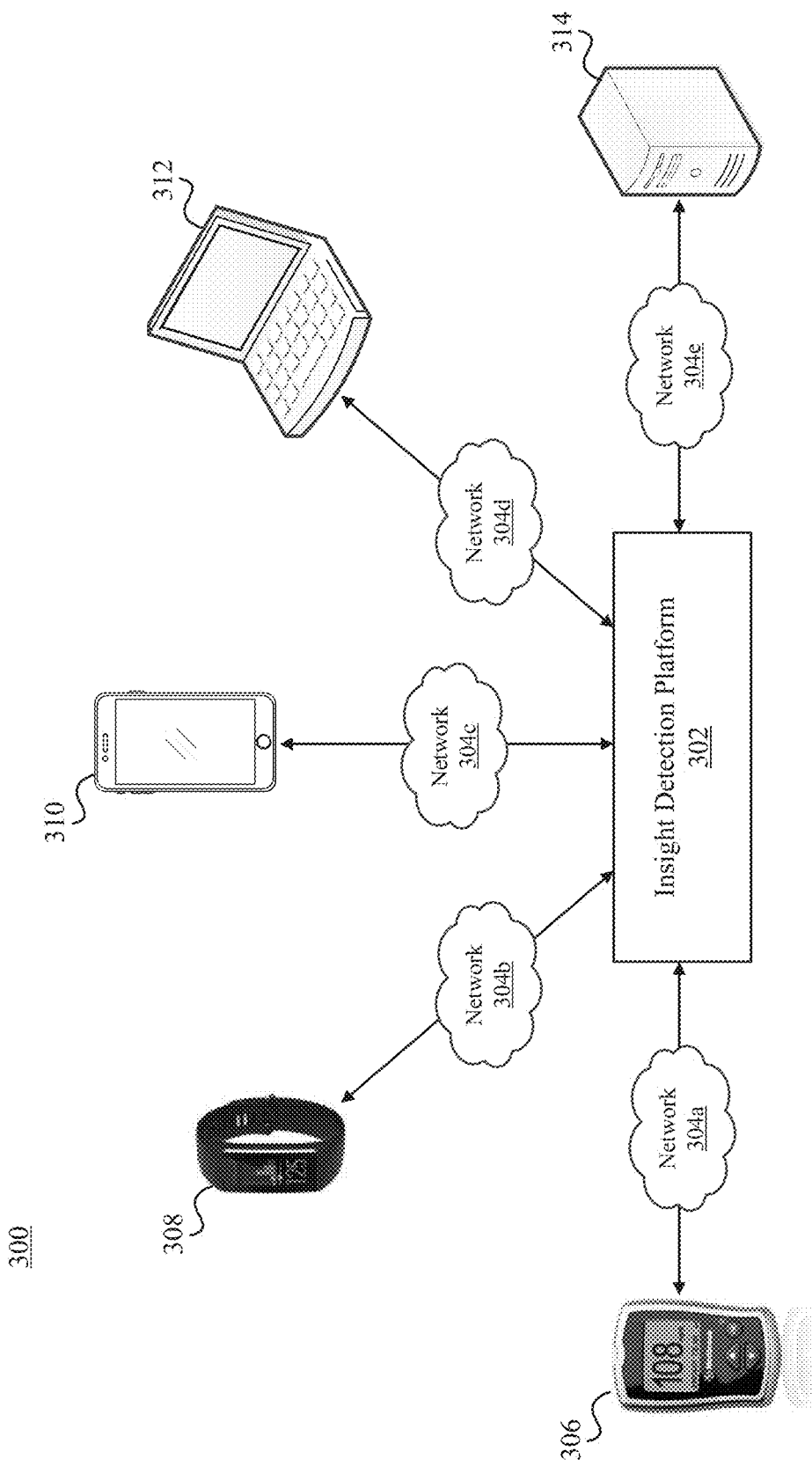
FIG. 3 depicts an example of a network environment that includes an insight detection platform that receives data from several different sources.

FIG. 3 depicts an example of a network environment 300 that includes an insight detection platform 302 that receives data from several different sources. Here, for example, the insight detection platform 302 receives data from a glucose monitoring device 306, fitness tracker 308, mobile phone 310, laptop computer 312, and network-accessible server system 314 (collectively referred to as the "networked devices").

The networked devices can be connected to the insight detection platform 302 via one or more computer networks 304a-e. The computer network(s) 304a-e can include LANs, WANs, MANs, cellular networks, the Internet, etc. Additionally or alternatively, the networked devices may communicate with one another over a short-range communication protocol, such as Bluetooth® or Near Field Communication (NFC). For example, as noted above, the insight detection platform 302 may reside on the mobile phone 310. In such embodiments, data received from the mobile phone 310 need not traverse network 304c. However, the mobile phone 310 may be communicatively coupled to the fitness tracker 308 via a Bluetooth® channel, the glucose monitoring device 306 via a Wi-Fi channel, the network-accessible server system 314 via a cellular channel, etc.

Embodiments of the network environment 300 may include some or all of the networked devices. For example, some embodiments of the network environment 300 include an insight detection platform 302 that only receives data from the glucose monitoring device 306, the fitness tracker 308, and the mobile phone 310 on which the insight detection platform 302 resides. As another example, some embodiments of the network environment include an insight detection platform 302 that only receives data from the glucose monitoring device 306 and the mobile phone 310 on which the insight detection platform 302 resides.

The insight detection platform 302 can continually or periodically receive data from the networked devices. Generally, the networked devices provide different types of data. For example, the glucose monitoring device 306 may generate physiological data that specifies the blood glucose level of an individual. As another example, the fitness tracker 308 may generate activity data that specifies activities performed by the individual (e.g., swimming, running, or weightlifting) or provides a general indicator of activity level (e.g., in the form of a step count). As yet another example, the mobile phone 310 may generate location data, activity data, and/or engagement data.

Note, however, that the insight detection platform 302 can be configured to calculate expected glycemic responses independent of the existence of any particular data stream. For example, if foodstuff data temporarily becomes unavailable, then the insight detection platform 302 may use location data to discover which restaurant(s) have been visited (and thus what kind of food was likely consumed). Accordingly, the insight detection platform 302 may be able to predict expected glycemic responses regardless of whether certain data streams are permanently missing, temporarily broken/disrupted, etc.

Those skilled in the art will recognize that certain networked devices have been described for the purpose of illustration only. For example, the glucose monitoring device 306 may be a continuous glucose monitor (e.g., Medtronic Enlite® Sensor) or a blood glucose meter (e.g., Bayer Contour®). The fitness tracker 308, meanwhile, may be a Fitbit Charge® 2, Apple Watch®, Garmin Approach® X40, etc. Other examples of networked devices that can be communicatively coupled to the insight detection platform 302 include tablet computers, personal digital assistants (PDAs), network-connected ("smart") home appliances (e.g., televisions and speakers, such as Amazon Echo® and Google Home®), game consoles (e.g., Sony PlayStation® or Microsoft Xbox® game console), music players (e.g., Apple iPod Touch®), mobile gaming devices (e.g., Sony PSP®), television-connected devices (e.g., Roku®, Apple TV®, Google Chromecast®, Amazon FireStick®, Android TV®, Blu-ray Disc™ players), and virtual/augmented reality systems (e.g., head-mounted displays such as Oculus Rift® and Microsoft Hololens®).

FIG. 4 depicts a flow diagram of a process 400 for discovering the correspondence between glycemic responses and contextual events. Initially, an insight detection platform (e.g., insight detection platform 200 of FIG. 2) can acquire physiological data associated with an individual (step 401). The physiological data may, for example, be generated by a glucose monitoring device that monitors the blood glucose level of the individual. However, other health indicators could also be measured (e.g., blood pressure, heart rate, etc.).

The insight detection platform can analyze the physiological data to identify a glycemic response pattern according to at least a pattern-defining parameter (step 402). The pattern-defining parameter may be, for example, a variation in the physiological data exceeding a specified threshold. For example, if the physiological data pertains to blood glucose levels, then the insight detection platform can parse the physiological data to detect glycemic response events.

The insight detection can also acquire contextual data generated by one or more network-enabled devices (step 403). The contextual data may be acquired via polling, interrupts, or both. The network-enabled device(s) may be configured to monitor various aspects of the individual. As shown in FIG. 3, contextual data may be generated by glucose monitoring devices, fitness trackers, mobile phones, etc. Some contextual data may be transmitted to the insight detection platform via a network, while other contextual data may be directly uploaded to the insight detection platform. For example, if the insight detection platform resides on a mobile phone, then activity data generated by a fitness tracker may be transmitted via a Bluetooth® channel while location data generated by the mobile phone may be uploaded directly to the insight detection platform.

The insight detection platform can analyze the contextual data to identify a contextual event related to the glycemic response pattern (step 404). A contextual event can represent an activity or a circumstance that is related to the variation. These activities and/or circumstances may be referred to as "characteristics" that define the contextual event.

For example, the insight detection platform may examine whether one or more values of the physiological data exceed a specified threshold. As another example, identifying the contextual event may include recognizing a user message that explicitly or implicitly is indicative of the contextual event. An example of an implicit indication is uploading a meal image, while an example of an explicit indication is checking a form box that specifies a meal was eaten. As another example, identifying the contextual event may include detecting, based on a sensor data stream from an electronic device associated with the individual, a time window with a recognizable pattern different than data from a time immediately preceding the time window. As another example, identifying the contextual event may include recognizing a message, from an external computer system associated with a healthcare provider for the individual, indicative of the contextual event.

A personalized retrospective insight for the individual can be created by the insight detection platform by dynamically linking the glycemic response pattern with the contextual event (step 405). In some embodiments, the insight detection platform categorizes the personalized retrospective insight as a positive pattern trigger or a negative pattern trigger. The categorization may affect which action(s) are subsequently performed by the insight detection platform or some computing device associated with the individual (e.g., a mobile phone or wearable electronic device). Categorizing the personalized retrospective insight as a positive pattern trigger may prompt the execution of a first action, while categorizing the personalized retrospective insight as a negative pattern trigger may prompt the execution of a second action. Examples of actions include generating a notification to be presented to the individual or some other person, modifying a parameter of a healthcare/medication regimen, etc. These positive and negative pattern triggers may prompt the execution of similar or different actions.

The insight detection platform may also store the personalized retrospective insight in a database to create a historical record of personalized retrospective insights (step 406).

FIG. 5 depicts a flow diagram of a process 500 for promoting changes in behavior based on personalized retrospective insights identified by an insight detection platform (e.g., insight detection platform 200 of FIG. 2). Initially, the insight detection platform can access a historical record of personalized retrospective insights associated with an individual (step 501). The historical record of personalized retrospective insights may be created in accordance with process 400 of FIG. 4.

The insight detection platform can then monitor contextual data associated with the individual (step 502). In some embodiments the insight detection platform continually monitors the contextual data in real time, while in other embodiments the insight detection platform periodically monitors the contextual data. The insight detection platform may discover a contextual event that is substantially similar to a past contextual event (step 503). Generally, contextual events are considered substantially similar if they share at least one characteristic in common. For example, contextual events may be substantially similar if they pertain to the same geographical location, foodstuff, activity, etc.

Note, however, that the temporal relationship between the contextual event and the variation may vary. For example, when an individual consumes a foodstuff, the blood glucose level may increase rapidly. Here, the contextual event is the consumption of the foodstuff. As another example, when an individual fails to fulfill a medication prescription or administer medication, the blood glucose level may slowly increase over time. Here, the contextual event is the failure to fulfill the medication prescription and/or administer the medication. Thus, some contextual events may result in an immediate change in physiological data, while the effect(s) of other contextual events may not be immediately recognizable.

In some embodiments, the insight detection platform calculates a measure indicative of an expected variation in physiological data in response to the contextual event (step 504). The measure may be based on the actual variation in physiological data that is related to the past contextual event.

The insight detection platform may cause a notification to be presented to the individual that specifies the expected variation in physiological data, the actual variation in physiological data, or both (step 505). The notification could be a visual notification, an audible notification, a tactile notification, or any combination thereof. For example, if the insight detection platform resides on a mobile phone in the form of a mobile application, then the notification may be a push notification created by the mobile application. Those skilled in the art will recognize that notifications could also be delivered as e-mail messages, Short Message Service (SMS) messages (commonly referred to as "text messages"), etc.

Some embodiments of the insight detection platform facilitate the creation of location-based notifications. More specifically, a virtual geographic boundary (also referred to as a "geofenced area") may be defined around certain locations (e.g., restaurants). When an individual enters the geofenced area, the individual may be notified of past variations in physiological data. For example, in response to determining that the individual has entered a specified restaurant, the insight detection platform may generate a notification that specifies how prior consumption of foodstuff(s) at the specified restaurant affected blood glucose levels. These notifications may be intended to incentivize the individual into making more healthy decisions.

Unless contrary to physical possibility, it is envisioned that the steps described above may be performed in various sequences and combinations. For example, the insight detection platform may simultaneously develop personalized retrospective insights and present notifications as biofeedback.

Other steps may also be included in some embodiments. For example, as noted above, the insight detection platform may calculate a measure indicative of an expected variation in physiological data in response to a contextual event. Thereafter, the insight detection platform may monitor the physiological data to detect the actual variation in physiological data related to the contextual event. The insight detection platform may compare these values in an effort to improve its prediction abilities. More specifically, the insight detection platform may apply a learning algorithm to improve its ability to calculate measures indicative of expected variations. The learning algorithm may be a machine learning (ML) algorithm or an artificial intelligence (AI) algorithm.

For example, the insight detection platform may apply ML algorithm(s) to detect contextual events within data generated by network-enabled device(s). Rather than use rule-based schemes that are likely to be ineffective over time, a ML model can be produced that automatically correlates changes in the data to changes in physiological data. Thus, the insight detection platform may train data pairs including a time interval of contextual data and a label of a glycemic response pattern, and then run the data pairs through an ML pipeline (e.g., a neural network or deep leaning algorithm). Such action causes an ML model to be produced that can recognize time series data indicative of a glycemic response pattern.

Processing System

Figure 6:
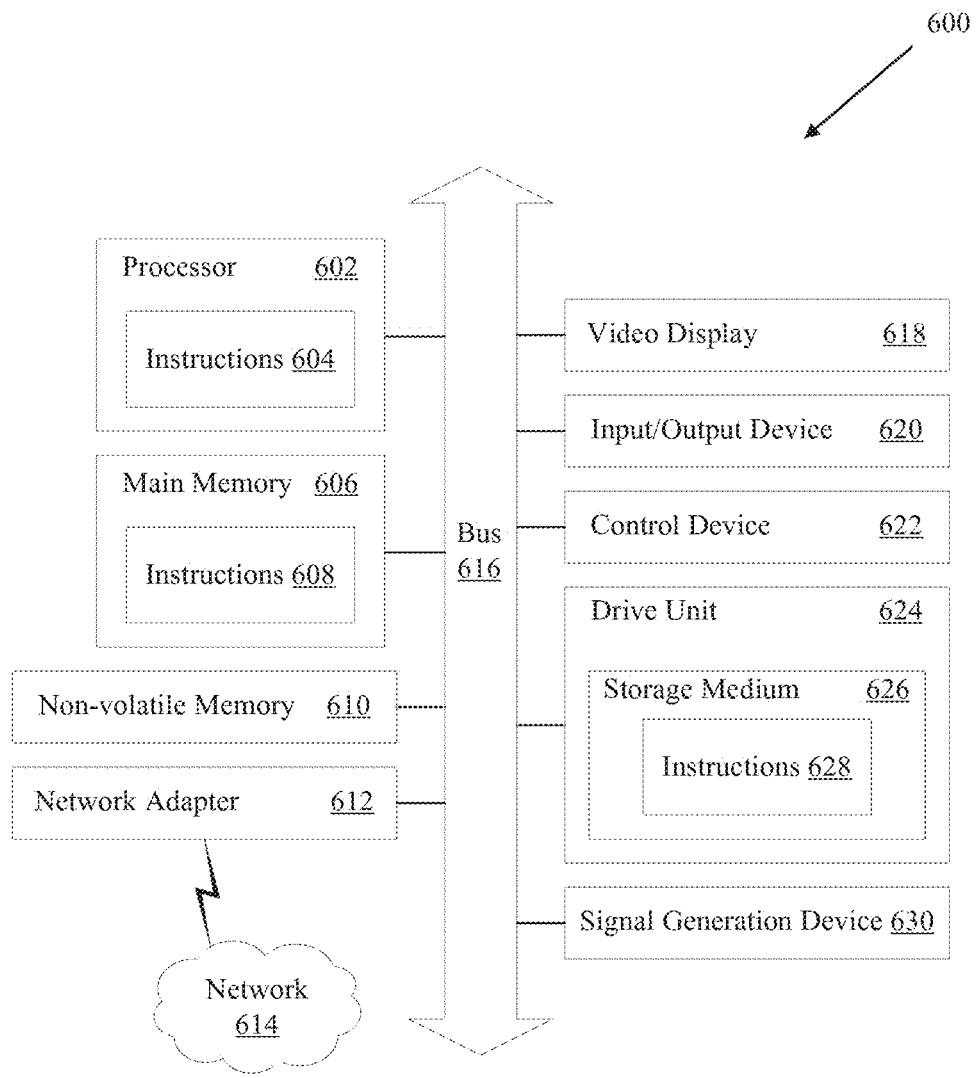
FIG. 6 is a block diagram illustrating an example of a processing system in which at least some operations described herein can be implemented.

FIG. 6 is a block diagram illustrating an example of a processing system 600 in which at least some operations described herein can be implemented. For example, some components of the processing system 600 may be hosted on a computing device that includes an insight detection platform.

The processing system 600 may include one or more central processing units ("processors") 602, main memory 606, non-volatile memory 610, network adapter 612 (e.g., network interface), video display 618, input/output devices 620, control device 622 (e.g., keyboard and pointing devices), drive unit 624 including a storage medium 626, and signal generation device 630 that are communicatively connected to a bus 616. The bus 616 is illustrated as an abstraction that represents one or more physical buses and/or point-to-point connections that are connected by appropriate bridges, adapters, or controllers. The bus 616, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 600 may share a similar computer processor architecture as that of a desktop computer, tablet computer, personal digital assistant (PDA), mobile phone, game console (e.g., Sony PlayStation® or Microsoft Xbox®), music player (e.g., Apple iPod Touch®), wearable electronic device (e.g., a watch or fitness tracker), network-connected ("smart") device (e.g., a television or home assistant device), virtual/augmented reality systems (e.g., a head-mounted display such as Oculus Rift® or Microsoft Hololens®), or another electronic device capable of executing a set of instructions (sequential or otherwise) that specify action(s) to be taken by the processing system 600.

While the main memory 606, non-volatile memory 610, and storage medium 626 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 628. The term "machine-readable medium" and "storage medium" shall also be taken to include any medium that is capable of storing, encoding, or carrying a set of instructions for execution by the processing system 600.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 604, 608, 628) set at various times in various memory and storage devices in a computing device. When read and executed by the one or more processors 602, the instruction(s) cause the processing system 600 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 610, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 612 enables the processing system 600 to mediate data in a network 614 with an entity that is external to the processing system 600 through any communication protocol supported by the processing system 600 and the external entity. The network adapter 612 can include a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 612 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
   acquiring physiological data generated by a glucose monitoring device that monitors a blood glucose level of an individual;
   analyzing the physiological data to identify a glycemic response according to at least a pattern-defining parameter;
   monitoring contextual data generated by one or more network-enabled devices,
      wherein the contextual data includes engagement data related to engagements with programs executing on a mobile phone, and
      wherein each engagement represents an interaction recorded by, or received on, the mobile phone;
   analyzing the contextual data to identify a first contextual event that is related to the glycemic response,
      wherein the first contextual event represents an engagement with a particular program executing on the mobile phone that is performed within a threshold duration of time with respect to the glycemic response;
   identifying a personalized retrospective insight for the individual by dynamically linking the glycemic response and the first contextual event;
   storing the personalized retrospective insight in a database to create a historical record of personalized retrospective insights associated with the individual;
   analyzing the contextual data to identify a second contextual event that is substantially similar to the first contextual event; and
   causing a notification to be presented to the individual that specifies the glycemic response experienced in combination with the first contextual event.

2. The computer-implemented method of claim 1, wherein the contextual data is acquired via polling, interrupts, or any combination thereof, and wherein said monitoring is performed continuously.

3. The computer-implemented method of claim 1, wherein said analyzing the physiological data comprises:
   examining one or more values of the physiological data that exceed a specified threshold.

4. The computer-implemented method of claim 1, further comprising:
   categorizing the personalized retrospective insight as a positive pattern trigger or a negative pattern trigger,
      wherein categorizing the personalized retrospective insight as the positive pattern trigger prompts execution of a first action, and
      wherein categorizing the personalized retrospective insight as the negative pattern trigger prompts execution of a second action.

5. The computer-implemented method of claim 1, further comprising:
   calculating a measure indicative of an expected glycemic response to the second contextual event,
      wherein the notification further specifies the calculated measure.

6. The computer-implemented method of claim 1, wherein said monitoring is continually performed to detect changes in the contextual data in real time, wherein said identifying the second contextual event is performed responsive to said monitoring, and wherein said causing the notification is performed responsive to said discovering.

7. The computer-implemented method of claim 1, wherein the glucose monitoring device is a continuous glucose monitor.

8. The computer-implemented method of claim 1, wherein the contextual data further includes:
   foodstuff data related to an identify or a quantity of a foodstuff consumed by the individual,
   location data related to a location of the individual,
   activity data related to a physical activity performed by the individual,
   medication data related to a medication event associated with the individual, or
   any combination thereof.

9. The computer-implemented method of claim 8, wherein the location data is generated by a first electronic device associated with the individual, wherein the activity data is generated by a second electronic device associated with the individual, and wherein the first electronic device and the second electronic device are different electronic devices.

10. The computer-implemented method of claim 8, wherein the medication data is acquired from a network-accessible digital storage associated with a healthcare entity.

11. The computer-implemented method of claim 8, further comprising:
receiving an image of a foodstuff consumed by the individual;
performing image recognition on the image to identify a feature of the foodstuff; and
generating the foodstuff data based on the feature.

12. The computer-implemented method of claim 1, wherein identifying the first contextual event or the second contextual event includes:
recognizing a user message that explicitly or implicitly is indicative of a contextual event;
detecting, based on a sensor data stream from a network-enabled device associated with the individual, a time window in the sensor data stream with a recognizable pattern different than data corresponding to a time immediately preceding the time window; or
recognizing a message, from an external computer system associated with a healthcare provider for the individual, indicative of a contextual event.

13. A computer-implemented method comprising:
acquiring physiological data generated by a glucose monitoring device that monitors a blood glucose level of an individual;
analyzing the physiological data to identify a glycemic response defined by a variation in the physiological data that exceeds a threshold;
acquiring contextual data that includes engagement data related to engagements with programs executing on a mobile phone associated with the individual,
wherein each engagement represents a separate interaction recorded by, or received on, the mobile phone;
analyzing the contextual data to identify a first contextual event that is related to the glycemic response,
wherein the first contextual event represents an engagement with a particular program executing on the mobile phone that is performed within a threshold duration of time with respect to the glycemic response;
identifying a personalized retrospective insight for the individual by dynamically linking the glycemic response and the first contextual event; and
storing the personalized retrospective insight in a database to create a historical record of personalized retrospective insights associated with the individual.

14. The computer-implemented method of claim 13, further comprising:
analyzing the contextual data to identify a second contextual event that is substantially similar to the first contextual event; and
causing a notification to be presented to the individual that specifies the glycemic response experienced in combination with the first contextual event.

* * * * *